US00PP35953P2

(12) United States Plant Patent
Smit

(10) Patent No.: US PP35,953 P2
(45) Date of Patent: Jul. 2, 2024

(54) ***PEPEROMIA* PLANT NAMED 'EC-PEPE-2302'**

(50) Latin Name: *Peperomia albovittata*
Varietal Denomination: EC-PEPE-2302

(71) Applicant: Eden Collection, BV, Sappemeer (NL)

(72) Inventor: Obed Smit, Sappemeer (NL)

(73) Assignee: Eden Collection B.V. (NL)

( * ) Notice: Subject to any disclaimer, the term of this patent is extended or adjusted under 35 U.S.C. 154(b) by 0 days.

(21) Appl. No.: 18/373,997

(22) Filed: Sep. 28, 2023

(51) Int. Cl.
*A01H 5/12* (2018.01)
*A01H 6/00* (2018.01)

(52) U.S. Cl.
USPC ..... Plt./373
CPC ..... *A01H 6/00* (2018.05)

(58) Field of Classification Search
USPC ..... Plt./373
CPC ..... A01H 5/12; A01H 5/00
See application file for complete search history.

*Primary Examiner* — Kent L Bell
(74) *Attorney, Agent, or Firm* — Cassandra Bright

(57) ABSTRACT

A new and distinct cultivar of *Peperomia* plant named 'EC-PEPE-2302' is disclosed, characterized by rounded-cordate leaves with a grey-green upper leaf surface color with dark purple veins and light green under surface color. Plants have a compact habit and veins are furrowed. The new variety is a *Peperomia*, typically used as an ornamental plant.

2 Drawing Sheets

Figure 1:
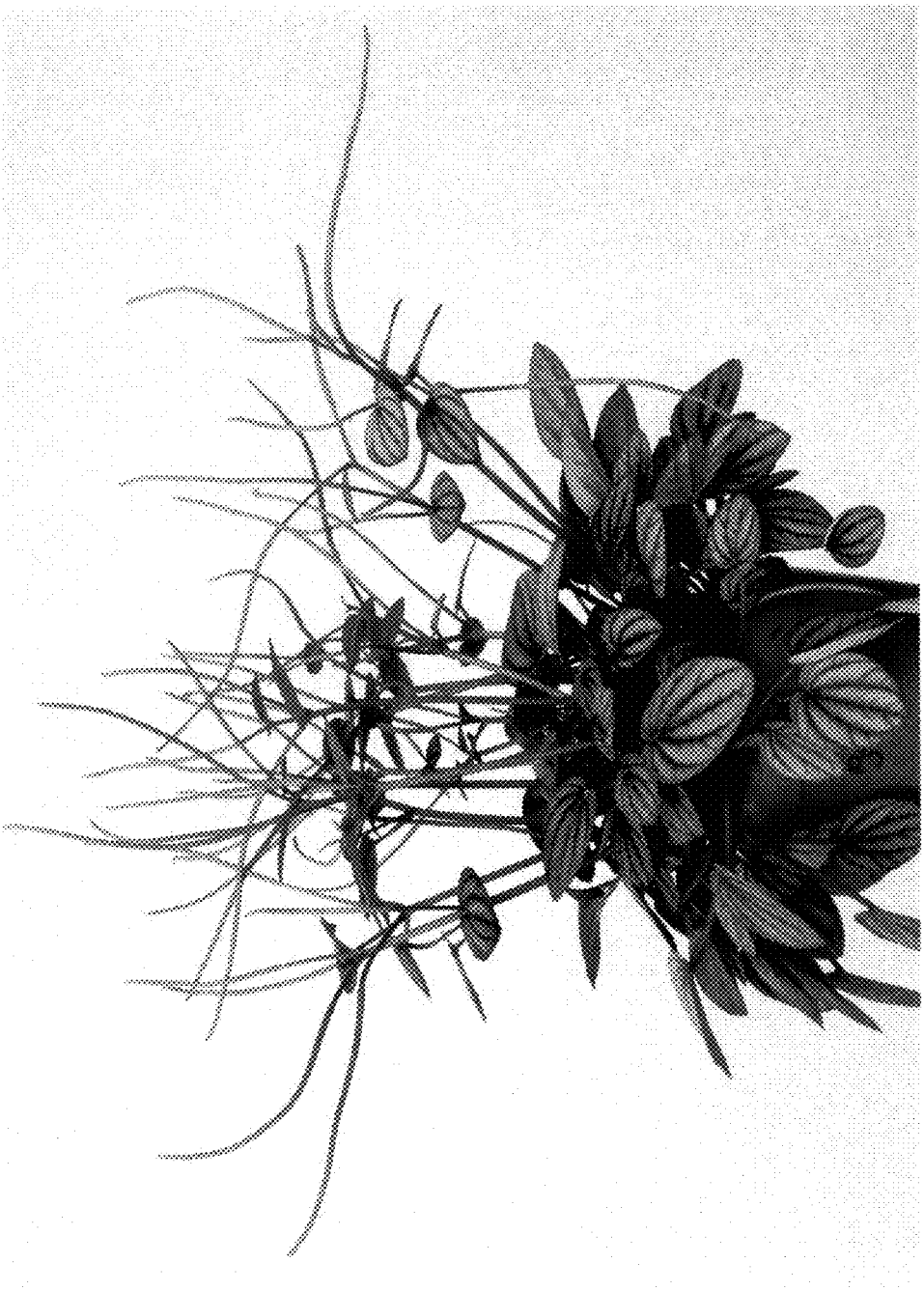

Latin name of the genus and species: *Peperomia albovittata.*

Variety denomination: 'EC-PEPE-2302'.

BACKGROUND OF THE INVENTION

The new cultivar is a product of a planned breeding program to produce distinct and better performing *Peperomia* varieties. The new variety was selected as a seedling resulting from the crossing of the seed parent, *Peperomia albovittata* '1628', and the pollen parent, *Peperomia albovittata* '1607', two unpatented varieties from the inventor's breeding line. The crossing was made by the inventor, Obed J. Smit, a citizen of the Netherlands in 2018. 'EC-PEPE-2302' was selected by the inventor in 2019 at a commercial greenhouse in Sappemeer, the Netherlands.

Asexual reproduction of the new cultivar 'EC-PEPE-2302' was first performed by leaf cuttings in Sappemeer, the Netherlands at a commercial greenhouse in September of 2019, and has shown that the unique features of this cultivar are stable and reproduced true to type through successive generations.

SUMMARY OF THE INVENTION

The cultivar 'EC-PEPE-2302' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'EC-PEPE-2302'. These characteristics in combination distinguish 'EC-PEPE-2302' as a new and distinct *Peperomia* cultivar:

1. Grey-Green upper leaf surface color with dark purple veins and light green under surface color.
2. Rounded cordate leaves.

3. Compact plant habit.
4. Furrowed veins.

PARENT COMPARISON

Plants of the new cultivar 'EC-PEPE-2302' are similar to plants of the seed parent in most horticultural characteristics, however, plants of the new cultivar 'EC-PEPE-2302' differ from '1628' in the following characteristics:

1. Foliage color of the upper surface of 'EC-PEPE-2302' is grey-green with dark purple veins; upper surface color of the seed parent is dark green with brown veins.
2. Leaves of the new variety are smaller than leaves of the seed parent variety.
3. Plants of the new variety are smaller and more compact than plants of the seed parent.

Plants of the new cultivar 'EC-PEPE-2302' are similar to plants of the pollen parent in most horticultural characteristics, however, plants of the new cultivar 'EC-PEPE-2302' differ from '1607' in the following characteristics:

1. Foliage color of the upper surface of 'EC-PEPE-2302' is grey-green with dark purple veins; upper surface color of the pollen parent is dark green with brown veins.
2. Leaves of the new variety are smaller than leaves of the pollen parent variety.
3. Plants of the new variety are smaller and more compact than plants of the pollen parent.

COMMERCIAL COMPARISON

Plants of the new cultivar 'EC-PEPE-2302' are similar to plants of the commercial variety *Peperomia* 'EC-PEPE-1803', U.S. Plant Pat. No. 31,278. However, plants of the new cultivar differ in the following characteristics:

1. Leaves of the new variety are larger (6.9 cm long, 6.0 cm wide) than leaves of this comparator (4.4 cm long, 3.7 cm wide).

2. Plants of the new variety are almost twice as wide (46.5 cm) as plants of this comparator (24.5 cm).
3. Dark vein coloration of the new variety is more closely held to the veins than the dark vein coloration of this comparator which bleeds farther into the leaf blade.

Plants of the new cultivar 'EC-PEPE-2302' are similar to plants of *Peperomia* 'Eden Rosso' U.S. Plant Pat. No. 24,379. However, plants of the new cultivar differ in the following characteristics:

1. Leaves of the new variety are light green on the lower surface; leaves of this comparator are red on the lower surface.
2. Plants of the new variety are larger than plants of this comparator.
3. Foliage of the new variety is more rounded than foliage of this comparator.

BRIEF DESCRIPTION OF THE PHOTOGRAPHS

The accompanying photograph in FIG. 1 illustrates in full color a typical plant of 'EC-PEPE-2302' grown in a greenhouse. The plant is approximately 52 weeks of age with inflorescences. Pot size of the photographed plant is 15 cm.

Figure 2:
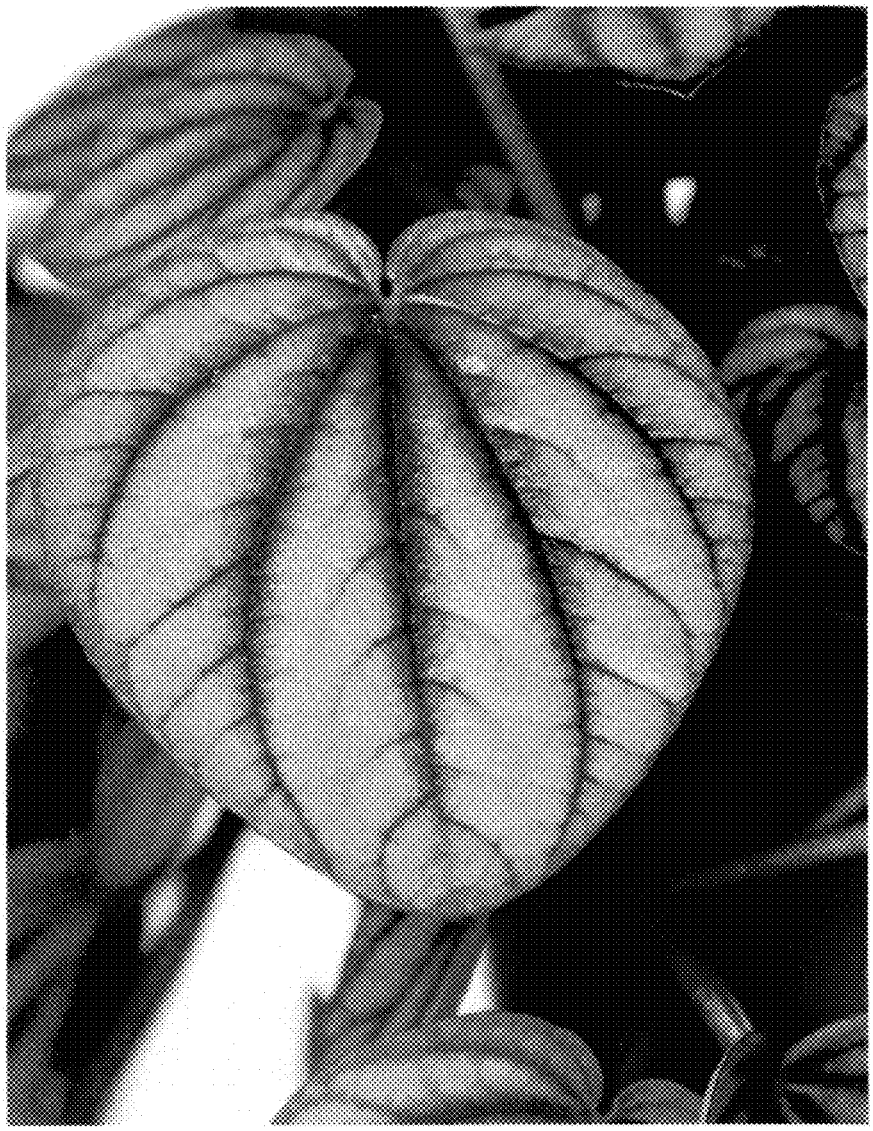

FIG. 2 illustrates a close up of the foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'EC-PEPE-2302' plants at 52 weeks of age, grown in a 15 cm pot in a greenhouse in Sappemeer, the Netherlands during December. The growing temperature ranged from 17° C. to 18° C. at night to 19° C. to 21° C. during the day. Measurements and numerical values represent averages of typical flowering types.

Botanical classification: *Peperomia albovittata* 'EC-PEPE-2302'.

PROPAGATION

Time to initiate roots: About 21 to 28 days at approximately 21° C.

Time to produce rooted cutting: About 100 to 120 days at 21° C.

Description of roots: Fibrous, fine, moderately dense, freely branching. White in color, not accurately measured with RHS chart.

PLANT

Plant type: Perennial potted plant.

Plant shape: Flattened globular with inflorescences growing above the foliage.

Growth habit: Rosettes of leaves, forming very short, thick stems.

Plant spread: Approximately 46.5 cm.

Height: 12.8 cm to top of foliar plane. 36 cm to top of floral plane.

Growth rate: Moderate.

Plant vigor: Moderate to high.

Age of plant described: Approximately 52 weeks.

Branching habit: Leaves in rosettes, eventually forming very short, thick stems, no lateral branches.

Pinching: Pinching not required.

Number of primary (main) branches per plant: Average 18.

Number of secondary (lateral) branches per plant: None.

Main branches:

*Length.*—Average: 2.2 cm.

*Diameter.*—Average: 0.2 cm.

Internode length: Average: Less than 0.2 cm.

Appearance and shape: Succulent, thick and rounded.

Luster: Moderately glossy.

Aspect/angle from vertical: Average angle: 30°.

Strength: Moderately strong.

Color:

*Developing.*—RHS Yellow-Green 148B.

*Mature.*—RHS Greyed-Green 197A.

*At internodes.*—RHS Greyed-Green 197A.

Pubescence: None.

Plant fragrance: None.

FOLIAGE

Leaf:

*Arrangement.*—Alternate, single.

*Quantity per rosette.*—Average 10.

*Average length.*—6.9 cm.

*Average width.*—6.0 cm.

*Shape of blade.*—Rounded cordate.

*Apex.*—Acute.

*Base.*—Cordate.

*Margin.*—Entire.

*Texture of top surface.*—Glabrous, smooth, moderately leathery.

*Texture of bottom surface.*—Glabrous, smooth, moderately leathery.

*Pubescence.*—None.

*Luster, upper side.*—Moderately glossy.

*Luster, under side.*—Matte.

*Color.*—Young foliage upper side: RHS Greyed-Green 191B blended with Yellow-Green 147B. Veins Brown 200B. Young foliage under side: Yellow-Green 148C. Mature foliage upper side: Near RHS Greyed-Green 191B, veins 147A mixed with N189A. Mature foliage under side: Yellow-Green 147D and 148D.

*Venation.*—Pattern: Parallel, furrowed. Venation color upper side: Yellow-Green 147A mixed with Greyed-Purple N189A. Venation color under side: RHS Yellow-Green 148B.

*Petiole.*—Average Length: 10.9 cm. Diameter: 0.4 cm. Texture: Glabrous, smooth. Luster: Both sides moderately glossy. Strength: Low. Color, upper side: RHS Yellow-Green 148C, strongly striped and marbled Greyed-Purple 181A. Color, under side: RHS Yellow-Green 148D, strongly striped and marbled Greyed-Purple 181B.

FLOWER

Inflorescence:

*Arrangement.*—Axillary compound spike.

*Inflorescence type and form.*—Spike.

*Inflorescence height.*—Average: 14.4 cm (excl. peduncle).

*Inflorescence diameter.*—Average: 0.3 cm.

*Quantity of flowers per inflorescence.*—Average approximately 1000 individual flowers per spike.

*Inflorescences per plant.*—Average 25.

Flower bud:

*Flower bud length.*—About 0.4 mm.

*Flower bud diameter.*—About 0.4 mm.

*Flower bud shape.*—Flattened orbicular.

*Flower bud texture.*—Glabrous, smooth.

*Flower bud luster.*—Matte.

*Flower bud color.*—Near Yellow-Green 145B, center Green 143A.

Flower:

*Flower type and form.*—Individual flowers are very small and consist of 1 bract 2 stamens and a single pistil. No petals or sepals present.

*Fragrance.*—No fragrance.

*Flower height (vertical).*—Average: 1 mm.

*Flower diameter (horizontal).*—Average: 0.6 mm.

*Aspect.*—Outwardly facing.

*Flower longevity on plant.*—Average one month.

*Persistent of self-cleaning?.*—Self-cleaning.

Petals: No petals present.

Calyx: No sepals present; no calyx present.

Peduncles:

*Terminal peduncle length.*—Average: 16.5 cm.

*Secondary peduncle length.*—Average 20.3.

*Terminal peduncle diameter.*—Average: 4.0 mm.

*Secondary peduncle diameter.*—Average 2 mm.

*Peduncle angle to lateral branch axis.*—Average angle: 20° Average range 20° to 50°.

*Peduncle strength.*—Weak.

*Peduncle texture.*—Glabrous, smooth.

*Peduncle luster.*—Slightly glossy.

*Peduncle color.*—Yellow-Green 147C, heavily very finely striped and marbled Greyed-Red 182A.

Pedicels: No pedicels present, individual flowers sessile.

Floral bracts: Below each individual flower a single bract is present, shaped orbicular, average length and width: 0.5 mm, colored near Green 143C.

Other structures: At the peduncle axils, 2 leaf-like bracts are present, shaped cordate, top acute, base cordate to oblique, average length: 5.0 cm, average width: 3.6 cm, both sides smooth, glabrous, upper side colored greyed-green; a blend of N189D and 198A, veined yellow-green to greyed-purple; a blend of 147A and N189A, under side yellow-green; N148D, veined darker; 148A. Bracts petiolate, average length of petiole: 1.4 cm, petioles u-shaped, average width at widest (horizontal): 0.35 cm, average width at narrowest (vertical): 0.2 cm, both sides smooth, glabrous, upper side colored yellow-green; 147D, strongly tinged greyed-red; 182A, under side yellow-green; 147D, slightly tinged greyed-red; 182A and 182B.

Reproductive organs:

Androecium:

*Number of stamens per flower.*—Average: 2.

*Filament length.*—Average: 0.75 mm.

*Filament color.*—Near Yellow-Green 145C.

*Anther shape.*—Kidney-shaped.

*Anther length.*—Average: 0.2 mm.

*Anther width.*—Average: 0.15 mm.

*Anther color.*—Near 160D.

*Amount of pollen.*—Low.

*Pollen color.*—White N155A.

Gynoecium:

*Pistil number (per flower).*—1.

*Pistil length.*—Average: 0.2 mm.

*Stigma shape.*—Flattened disc.

*Stigma length.*—Average: 0.5 mm.

*Stigma diameter.*—Average: 0.3 mm.

*Stigma color.*—Near RHS Yellow-Green 152D.

*Style length.*—No style visible, stigma sessile.

*Ovary color.*—Near RHS Green 143C.

OTHER CHARACTERISTICS

Seeds and fruits: None observed to date.

Disease/pest resistance: No increased nor decreased resistance nor susceptibility to normal diseases and pests of *Peperomia* has been observed.

Temperature tolerance: Tolerates temperatures up to 40° C. Hardy to USDA zones 10 to 12.

What is claimed is:

1. A new and distinct cultivar of *Peperomia* plant named 'EC-PEPE-2302' as herein illustrated and described.

* * * * *